United States Patent
Duflot et al.

(12)

(10) Patent No.: US 6,268,190 B1
(45) Date of Patent: Jul. 31, 2001

(54) METHOD OF PRODUCING ARABITOL BY CONTINUOUS FERMENTATION

(75) Inventors: Pierrick Duflot, La Couture; Pierre Lanos, La Bassee; Fabrice Machu, Locon; Laurent Segueilha, Lambersart, all of (FR)

(73) Assignee: Roquette Freres, Lestrem (FR)

( * ) Notice: Subject to any disclaimer, the term of this patent is extended or adjusted under 35 U.S.C. 154(b) by 0 days.

(21) Appl. No.: 09/567,386

(22) Filed: May 9, 2000

(30) Foreign Application Priority Data

May 11, 1999 (FR) .................................................. 99 05995

(51) Int. Cl.$^7$ ....................................................... C12P 7/18
(52) U.S. Cl. ......................... 435/158; 435/171; 435/813; 435/911; 435/921; 435/930; 435/940
(58) Field of Search ..................................... 435/158, 813, 435/911, 930, 921, 940, 171

(56) References Cited

U.S. PATENT DOCUMENTS 2,986,495   5/1961   Hiroshi et al. .

FOREIGN PATENT DOCUMENTS 0 327 342   8/1989   (EP) .

OTHER PUBLICATIONS

Van Zyl P.J. et al.., 1990, vol. 33, No. 1, pp 12–17, XP000866383.

Primary Examiner—Herbert J. Lilling
(74) Attorney, Agent, or Firm—Henderson & Sturm LLP

(57) ABSTRACT

A method of producing arabitol by continuous fermentation of at least one sugar by micro-organisms producing arabitol, characterised in that arabitol is produced in a first fermentation area including at least one fermenter in such a manner that some of the sugar introduced into the fermentation medium is consumed by said micro-organisms, some of the fermentation medium obtained in this way is transferred into a second fermentation area including at least one fermenter, the volume being maintained constant in the first fermentation area by adding sugar, production of arabitol continues in said second fermentation area in such a manner as to consume the residual sugar of the fermentation medium, the fermentation medium thus obtained from said second fermentation area is separated a continuously into a fraction concentrated in micro-organisms and another, soluble fraction enriched in arabitol, and the arabitol thus obtained is collected.

12 Claims, No Drawings

METHOD OF PRODUCING ARABITOL BY CONTINUOUS FERMENTATION

CROSS-REFERENCE TO RELATED APPLICATIONS

Not Applicable

STATEMENT REGARDING FEDERALLY SPONSORED RESEARCH OR DEVELOPMENT

Not Applicable

BACKGROUND OF THE INVENTION

FIELD OF THE INVENTION

The present invention relates to a method of producing arabitol by continuous fermentation of at least one sugar by micro-organisms producing arabitol.

It relates more particularly to a method of producing arabitol by continuous fermentation of at least one sugar by micro-organisms producing arabitol, employing at least two interconnected fermentation areas.

To be more precise, in the method according to the invention, arabitol is produced in a first fermentation area in such a manner that some of the sugar introduced into the fermentation medium that it contains is consumed, some of said fermentation medium is transferred into a second fermentation area, the volume of said first area being maintained constant by adding sugar, and production of arabitol continues in the second a fermentation area in such a manner as to consume the residual sugar.

Thereafter, in the second fermentation area, the fermentation medium with a low residual sugar content obtained in this way is separated into a fraction concentrated in micro-organisms and another, soluble fraction rich in arabitol, possibly with recycling of said micro-organisms to the entry of the first fermentation area.

The industrial preparation of arabitol is based mainly on fermentation processes.

Generally speaking, micro-biological methods of producing arabitol can employ two different fermentation modes: a batch mode and a continuous mode.

In the batch mode, two techniques are conventionally used: the batch fermentation technique and the fed batch fermentation technique.

In the batch fermentation technique, all the substrates necessary for feeding the micro-organisms are introduced at the beginning of the fermentation and the arabitol produced is extracted at the end of fermentation.

The term "substrates" refers to all the nutrients that are introduced into the fermentation medium. In the context of the invention, the substrates are mainly carbonaceous sources (including sugar) and nitrogenous sources which can be assimilated directly by the arabitol-producing micro-organisms.

However, this continuous fermentation technique has the drawbacks of requiring long fermentation times to enable total consumption of the sugar introduced into the fermentation medium and of necessitating the use of large volumes of fermentation medium, and therefore large fermenters, to obtain satisfactory conversion yields. This leads to a mediocre productivity per unit volume.

Moreover, variation of the concentration of one of the ingredients of the fermentation medium can affect the arabitol yield or productivity.

One solution is to use the second batch fermentation technique, known as fed batch fermentation.

In particular, this technique introduces the substrates progressively into the fermentation medium.

The advantage of this technique is that the substrate concentration in the fermentation medium can be controlled and all the sugar can be consumed.

Thus the fed batch fermentation technique solves problems associated with the potential inhibiting effects of some ingredients of the fermentation substrates on the growth of the micro-organisms or on the production of arabitol or, for example provides finer adjustment of the aeration that conditions arabitol production.

However, to obtain satisfactory yield and productivity, it is necessary to use high substrate concentrations. Most importantly, the fermentation times are long and the various fermentation steps require complex and painstaking control.

The method described by ESCALANTE et al. (in Journal of Fermentation and Bioengineering, 70–4, 228–231, 1990) for the production of arabitol by Hansenula using fed batch fermentation cannot achieve industrially viable yield and productivity.

This is because, although arabitol is selectively produced, and although the fed batch fermentation process ensures that all of the glucose introduced into the fermentation medium is consumed, arabitol is obtained with a yield of the order of only 14%.

The second fermentation mode conventionally used for the biological production of arabitol is the continuous mode, as described by JAKOBUS van ZYL and PRIOR in Appl. Microbiol. Biotechnol. (1990), 33, 12–17, for example.

In continuous mode, all the fermentation substrates are added continuously to the fermenter and fractions of the fermentation medium are extracted at the same flowrate as the introduction of substrates, to maintain a constant working volume.

This fermentation mode significantly increases yield and productivity but does not produce a product of high purity because the arabitol drawn off is necessarily contaminated by the substrates re-introduced during fermentation.

Consequently, the major drawback of continuous mode fermentation processes is the need to purify the arabitol. Also, available purification techniques can separate the arabitol from the residual sugar not assimilated by the micro-organisms only with difficulty.

For this reason, complex, large and costly purification installations are conventionally associated with these continuous fermentation processes.

Fermentation experts therefore devote all their efforts to seeking operating conditions which can reconcile improved arabitol yield and productivity with a low residual sugar content enabling easy and low-cost purification of the arabitol produced.

Thus the aim of the present invention is to solve the problem of producing arabitol of satisfactory purity with excellent yield and productivity by employing a particular continuous fermentation technique.

The method of producing arabitol developed by the Applicant company consists of fermenting at least one sugar using arabitol-producing micro-organisms in two fermentation areas.

The invention relates more particularly to a method of producing arabitol by continuous fermentation of at least one sugar by micro-organisms producing arabitol, characterised in that:

a) arabitol is produced in a first fermentation area including at least one fermenter in such a manner that some of the sugar introduced into the fermentation medium is consumed by said micro-organisms, b) some of the fermentation medium obtained in this way is transferred into a second fermentation area including at least one fermenter, the volume being maintained constant in the first fermentation area by adding sugar, c) production of arabitol continues in said second fermentation area in such a manner as to consume the residual sugar of the fermentation medium, d) the fermentation medium thus obtained from said second fermentation area is separated continuously into a fraction concentrated in micro-organisms and another, soluble fraction enriched in arabitol, and e) the arabitol thus obtained is collected.

The first step of the process according to the invention consists of producing arabitol in a first fermentation area comprising at least one fermenter in such a manner that part of the sugar introduced into the fermentation medium is consumed by said micro-organisms.

The micro-organisms are advantageously selected from natural or modified osmosis-tolerant yeasts producing arabitol from sugar as a directly assimilable source of carbon.

The term "osmosis-tolerant yeasts" refers to yeasts which can withstand high osmotic pressures and are of the genus Yamadazyma, Debaromyces, Hansenula, Candida, Zygosaccharomyces or Saccharomyces. The above list is not limiting on the invention.

The term "natural osmosis-tolerant yeasts" refers to osmosis-tolerant yeasts which are isolated from their environment for their natural capacity for producing a given metabolite, here arabitol.

The term "modified osmosis-tolerant yeasts" refers to osmosis-tolerant yeasts whose natural capacity for producing a given metabolite, here arabitol, has been optimised by the use of random or controlled mutagenesis techniques or the techniques of molecular biology.

The term "sugar" refers in the context of the present invention to all carbonaceous sources which can be assimilated directly by the arabitol-producing micro-organisms.

The sugar is selected from the group consisting of glucose, galactose, sucrose, arabinose, glycerol, fructose, maltose, xylulose, ribulose, mannitol, myo-inositol, ethanol, starch and maltose, for example, alone or in combination.

The first fermentation area is adapted to provide a high production of arabitol by encouraging the consumption of some of the sugar introduced into the fermentation medium.

In the context of the invention, the expression "some of the sugar" means at least 50 wt. % of the sugar, preferably at least 80 wt. % and even more preferably at least 90 wt. %.

In a preferred first embodiment of the method according to the invention, production of arabitol is initiated in the first fermentation area in the batch mode, and all the fermentation substrates, including the sugar, and the micro-organisms are introduced simultaneously.

In a second preferred embodiment of the method according to the invention, production of arabitol is initiated in the first fermentation area in the fed batch mode and the arabitol-producing micro-organisms are fed with sugar progressively.

A fed batch mode is advantageously chosen to start fermentation in the method according to the invention.

This batch feeding mode progressively fills the first fermentation area with substrates to maintain a high rate of growth of the micro-organisms, good conversion of the sugar into arabitol and a sugar concentration in the fermentation medium tolerated by the arabitol-producing micro-organism concerned.

The expression "sugar concentration tolerated by the micro-organism" refers to a minimum sugar concentration which does not inhibit either the growth of said micro-organism or its production of arabitol.

Generally speaking, for all arabitol-producing micro-organisms, the process conditions are adjusted to avoid total consumption of the sugar.

The high production of arabitol in the first fermentation area generally leads to relatively high quantities of unconsumed residual sugar, depending on the micro-organisms used. As a general rule, the residual sugar content is at least 2.5 wt. %.

The second step of the method according to the invention then consists of transferring some of the fermentation medium obtained in this way into a second fermentation area comprising at least one fermenter, the volume being maintained constant in the first fermentation area by adding sugar.

Thus some of the fermentation medium is transferred from the first fermentation area to the second fermentation area when said fermentation medium has been enriched with arabitol but still contains unconsumed residual sugar in an amount which renders purification of the arabitol produced complex and costly.

This transfer is accompanied by continuous feeding of sugar into the first fermentation area, not only to maintain the volume constant, but also, and most importantly, to continue the production of arabitol with a productivity and a conversion yield at least equal to the values obtained during the arabitol production initiation phase described above.

The first fermentation area is advantageously continuously fed with the substrates, rather than with sugar, as described hereinafter.

The third step of the method according to the invention consists of continuing the production of arabitol in the second fermentation area in such a manner as to consume the residual sugar in the portion of the fermentation medium from the first fermentation area.

The second fermentation area is therefore used both to continue the production of arabitol and also, and most importantly, to complete the consumption of the sugar contaminating the portion of the fermentation medium transferred from the first fermentation area to the second fermentation area in such a manner as to leave only a low residual sugar content.

A low residual sugar content advantageously means a sugar concentration in the fermentation medium not greater than 2 wt. % and preferably not greater than 1 wt. %

In a preferred embodiment of the method according to the invention, this step is implemented in different size fermenters, the fermenters of the second fermentation area having a smaller volume than those of the first fermentation area.

In an even more preferred embodiment of the method according to the invention, there is only one fermenter in each fermentation area.

The fourth step of the method according to the invention consists of continuously separating the fermentation medium with a low residual sugar content obtained in this way into a fraction concentrated in micro-organisms and another, soluble fraction enriched in arabitol.

Continuous separation of the micro-organisms and the arabitol-enriched fraction is effected by any means known to the skilled person, for example by micro-filtration, using membranes with a pore diameter matched to the size of the micro-organism concerned, or by centrifuging at from 1000 to 10000 g, preferably by micro-filtration, as described hereinafter.

The arabitol-enriched clarified solution obtained at the end of the separation step constitutes the arabitol produced.

The Applicant company has also established that it can be advantageous to recycle the fraction enriched in micro-organisms to the entry of the first fermentation area.

The advantage of this micro-organism recycling step is to re-introduce a biomass whose fermentation capacities are complete and thereby to avoid the time-delay that would result from preparing a new culture of arabitol-producing micro-organisms.

The arabitol produced is recovered by concentration to a value of the order of 20% or more and this can be followed by a crystallisation step using any method known to the skilled person.

Other features and advantages of the invention will become apparent on reading the following non-limiting examples.

EXAMPLE 1

The two fermentation areas employed each included one fermenter, but the two fermenters were different sizes. The CHEMAP® first fermenter had a volume of 20 l (17 l usable capacity) and the second fermenter, which was of the same make, had a volume of 5 l (4 l usable capacity).

A pre-culture of the micro-organism *Yamadazyma ohmeri*, strain ATCC 20209, was first prepared in another 20 l fermenter.

The pre-culture medium contained 50 g/l of glucose, 8 g/l of corn steep liquor, 2 g/l of $KH_2PO_4$ and 1 g/l of $MgSO_4$. The pre-culture was prepared at 30° C., stirred at 600 rpm and aerated at 1 vvm for 12 h and the pH was regulated to 4.5 with 20% $NH_4OH$.

The fermenter of the first fermentation area was seeded with 1 l of the pre-culture. It was made up to 6 l with a medium containing 50 g/l of glucose, 8 g/l of corn steep liquor, 2.5 g/l of $KH_2PO_4$, 1 g/l of $MgSO_4$ and 0.05 g/l of $FeSO_4$.

The temperature was set to 30° C. The pH was regulated to 4.5 up to 35 h using 20% $NH_4OH$ and then to 3 using 5N KOH.

The glucose was added as shown in table I below. The biomass was estimated by measuring the absorbance (optical density OD) of the medium at 620 nm.

For *Yamadazyma ohmeri*, a unit of absorbance at 600 nm was equivalent to a biomass in the order of 0.2 g/l.

TABLE I

| Time (h) | OD | Glucose (g/l) | Arabitol (g/l) | Volume (l) | Added glucose |
|---|---|---|---|---|---|
| 0 | 14 | 50 | 0 | 6 | |
| 10 | 49 | 29 | 8 | 6 | 500 g in 5 l |
| 20 | 91 | 30 | 15 | 10 | 1 200 g in 5 l |
| 30 | 154 | 30 | 31 | 15 | 1 300 g in 3 l |
| 40 | 190 | 29 | 60 | 17 | |

After 40 h of fermentation, the usable volume of the fermenter in the first fermentation area was reached and the residual glucose concentration was 29 g/l.

4 l of the fermentation medium was then transferred from the first fermenter to the fermenter of the second fermentation stage and 800 g of glucose was then added in a volume of 2 l to the first fermenter. The temperature of the second fermentation area was set to 38° C. and the pH was regulated to 3.5 using 5N KOH.

The fermenters were then allowed to operate separately for 46 h, at which time the first sample of arabitol was taken from the second fermenter.

From 46 h the fermenter of the first fermentation area was fed with 250 g/l of glucose at a flowrate of the order of 0.4 l/h and with 50 g/l of corn steep liquor at a flowrate of the order of 10 ml/h.

The medium was transferred from the first fermentation area to the second using a PCM® pump and then from the second fermentation area to a MEMBRALOX® tangential filtration module from which were recovered a permeate rich in arabitol and a retentate rich in micro-organisms.

The retentate was then recycled to the entry of the first fermentation area.

To maintain the levels in the two fermenters the outflow of the permeate was made equal to the feed rate of the glucose.

The flowrate changed with time as a function of the rate of consumption of the glucose by the micro-organisms in the fermenters. Feeding was stopped at 200 h and the fermenter of the second fermentation area emptied.

Fermentation was allowed to continue in the fermenter of the first fermentation area for a further 10 h before treating the medium in the tangential filter module.

Table II below shows the measurements taken after transferring the fermentation medium from the first fermentation area to the second.

TABLE II

| | First fermenter | | | | Second fermenter | | |
|---|---|---|---|---|---|---|---|
| Time (h) | OD | Glucose (g/l) | Arabitol (g/l) | Volume (l) | OD | Glucose (g/l) | Arabitol (g/l) | Volume (l) |
| 40 | 190 | 29 | 60 | 17 | | | | |
| 40.1 | 165 | 75 | 57 | 15 | 190 | 28 | 61 | 4 |
| 46 | 170 | 39 | 74 | 15 | 190 | 10 | 74 | 4 |
| 60 | 173 | 25 | 95 | 15 | 175 | 5 | 102 | 4 |
| 80 | 177 | 26 | 107 | 15 | 174 | 6 | 115 | 4 |
| 100 | 182 | 25 | 111 | 15 | 183 | 4 | 119 | 4 |
| 120 | 184 | 25 | 113 | 15 | 186 | 5 | 123 | 4 |
| 140 | 191 | 27 | 112 | 15 | 190 | 6 | 121 | 4 |
| 160 | 193 | 25 | 108 | 15 | 194 | 6 | 119 | 4 |
| 180 | 194 | 28 | 105 | 15 | 189 | 7 | 114 | 4 |
| 200 | 201 | 25 | 102 | 15 | 194 | 9 | 110 | 4 |
| 210 | 198 | 1 | 115 | 15 | | | | |

Globally, 8.8 kg of arabitol was recovered and 18.7 kg of glucose was used, representing a yield of 47% and a productivity of 2.2 g/l/h.

In batch fermentation carried out under the same production medium conditions and with the same glucose feed the yield was 40% and the productivity was only 1.5 g/l/h.

The method according to the invention therefore achieved much better yield and productivity.

Also, the low residual glucose content meant that the arabitol recovered was of totally satisfactory purity.

EXAMPLE 2

Arabitol was prepared under the same fermentation conditions as example 1, but using the micro-organism *Yamadazyma ohmeri*, strain ATCC 20209, modified by the standard random ultraviolet mutagenic technique (employing at least one ultraviolet mutagenesis cycle with enrichment with nystatin), the strain being selected for its ability to produce arabitol with a yield 8 to 10 points higher than the mother strain.

After obtaining a pre-culture of said modified strain and transferring it into the first fermentation area as described in connection with example 1, glucose was added as set out in table III below.

TABLE III

| Time (h) | OD | Glucose (g/l) | Arabitol (g/l) | Volume (l) | Added glucose |
|---|---|---|---|---|---|
| 0 | 15 | 50 | 0 | 6 | |
| 10 | 50 | 19 | 8 | 6 | 500 g in 5 l |
| 20 | 102 | 31 | 15 | 10 | 1 200 g in 5 l |
| 30 | 164 | 29 | 36 | 15 | 1 300 g in 3 l |
| 40 | 204 | 28 | 70 | 17 | |

After 40 h of fermentation, the usable volume of the fermenter of the first fermentation area was reached and the residual glucose concentration was 28 g/l.

4 l of the fermentation medium was then transferred from the first fermenter to the fermenter of the second fermentation stage and 800 g of glucose was then added in a volume of 2 l to the first fermenter.

The temperature of the second fermentation area was set to 38° C. and the pH was regulated to 3.5 using 5N KOH.

The fermenters were then allowed to operate separately up to 46 h, at which time the first sample of arabitol was taken from the second fermenter.

From 46 h the fermenter of the first fermentation area was fed with 250 g/l of glucose at a flowrate of the order of 0.4 l/h and with 50 g/l of corn steep liquor at rate of the order of 10 ml/h.

Table IV below shows the measurements taken after transferring the fermentation medium from the first fermentation area to the second.

TABLE IV

| | First fermenter | | | | Second fermenter | | |
|---|---|---|---|---|---|---|---|
| Time (h) | OD | Glucose (g/l) | Arabitol (g/l) | Volume (l) | OD | Glucose (g/l) | Arabitol (g/l) | Volume (l) |
| 40 | 204 | 28 | 70 | 17 | | | | |
| 40.1 | 180 | 76 | 62 | 15 | 204 | 28 | 70 | 4 |
| 46 | 191 | 39 | 85 | 15 | 196 | 12 | 90 | 4 |
| 60 | 204 | 23 | 121 | 15 | 200 | 5 | 128 | 4 |
| 80 | 212 | 22 | 141 | 15 | 210 | 7 | 152 | 4 |
| 100 | 222 | 24 | 150 | 15 | 225 | 6 | 163 | 4 |
| 120 | 225 | 26 | 151 | 15 | 224 | 5 | 165 | 4 |
| 140 | 230 | 25 | 150 | 15 | 230 | 6 | 166 | 4 |
| 160 | 227 | 24 | 149 | 15 | 225 | 6 | 164 | 4 |
| 180 | 228 | 21 | 148 | 15 | 227 | 8 | 163 | 4 |
| 200 | 231 | 25 | 145 | 15 | 235 | 7 | 161 | 4 |
| 210 | 230 | 1 | 164 | 15 | | | | |

Globally, 12 kg of arabitol was recovered and 19 kg of glucose was used, representing a yield of 63% and a productivity of 4 g/l/h.

In batch fermentation carried out under the same production medium conditions and with the same glucose feed the yield was 55% and the productivity was only 2.5 g/l/h.

The method according to the invention therefore clearly improved yield and productivity.

Also, the low residual glucose content meant that the arabitol recovered was of totally satisfactory purity.

EXAMPLE 3

The two fermentation areas were operated as in example 1.

A pre-culture of the micro-organism *Candida polymorpha*, natural strain ATCC 20213, was first prepared in a 20 l CHEMAP® fermenter under the same conditions as for the *Y. ohmeri* strain of example 1.

The fermenter of the first fermentation area was seeded with 1 l of this pre-culture.

The quantity was made up to 6 l with a medium containing 50 g/l of glucose, 3 g/l of yeast extract, 2 g/l of $KH_2PO_4$ and 1 g/l of $MgSO_4$.

The temperature was set to 30° C. The pH was regulated to 4.5 up to 30 h using 20% $NH_4OH$ and then using 5N KOH.

The addition of glucose was controlled as shown in table V below.

The biomass was estimated by measuring the absorbance (optical density OD) of the medium at 620 nm.

For *Candida polymorpha*, a unit of absorbance at 600 nm was equivalent to a biomass in the order of 0.22 g/l.

TABLE V

| Time (h) | OD | Glucose (g/l) | Arabitol (g/l) | Volume (l) | Added glucose |
|---|---|---|---|---|---|
| 0 | 10 | 50 | 0 | 6 | |
| 10 | 45 | 21 | 3 | 6 | 500 g in 5 l |
| 20 | 85 | 27 | 8 | 10 | 1 200 g in 5 l |
| 30 | 144 | 33 | 19 | 15 | 1 300 g in 3 l |
| 40 | 174 | 30 | 30 | 17 | |

After 40 h of fermentation, the usable volume of the fermenter in the first fermentation area was reached and the residual glucose concentration was 30 g/l.

4 l of the fermentation medium was then transferred from the first fermenter to the fermenter of the second fermentation stage and 800 g of glucose was then added in a volume of 2 l to the first fermenter.

The temperature of the second fermentation area was set to 37° C. and the pH was regulated to 4.5 using 5N KOH.

The fermenters were then allowed to operate separately up to 46 h, at which time the first sample of arabitol was taken from the second fermenter.

From 46 h the fermenter of the first fermentation area was fed with 250 g/l of glucose at a flowrate of the order of 0.4 l/h and with 50 g/l of corn steep liquor at a flowrate of the order of 10 ml/h.

Table VI below shows the measurements taken after transferring the fermentation medium from the first fermentation area to the second.

TABLE VI

| | First fermenter | | | | Second fermenter | | |
|---|---|---|---|---|---|---|---|
| Time (h) | OD | Glucose (g/l) | Arabitol (g/l) | Volume (l) | OD | Glucose (g/l) | Arabitol (g/l) | Volume (l) |
| 40 | 174 | 30 | 30 | 17 | | | | |
| 40.1 | 150 | 77 | 27 | 15 | 174 | 29 | 30 | 4 |
| 46 | 160 | 44 | 34 | 15 | 174 | 14 | 36 | 4 |

TABLE VI-continued

| | First fermenter | | | | Second fermenter | | |
|---|---|---|---|---|---|---|---|
| Time (h) | OD | Glu-cose (g/l) | Ara-bitol (g/l) | Volume (l) | OD | Glucose (g/l) | Arabitol (g/l) | Volume (l) |
| 60 | 165 | 31 | 46 | 15 | 164 | 11 | 50 | 4 |
| 80 | 167 | 29 | 51 | 15 | 169 | 8 | 56 | 4 |
| 100 | 172 | 23 | 52 | 15 | 171 | 6 | 58 | 4 |
| 120 | 176 | 27 | 51 | 15 | 174 | 5 | 59 | 4 |
| 140 | 180 | 29 | 50 | 15 | 179 | 7 | 57 | 4 |
| 160 | 184 | 28 | 49 | 15 | 181 | 7 | 55 | 4 |
| 180 | 183 | 24 | 50 | 15 | 177 | 8 | 55 | 4 |
| 200 | 186 | 26 | 47 | 15 | 182 | 8 | 53 | 4 |
| 210 | 185 | 1 | 54 | 15 | | | | |

Globally, 4.1 kg of arabitol was recovered and 17.4 kg of glucose was used, representing a yield of 23.6% and a productivity of 1 g/l/h.

In batch fermentation carried out under the same production medium conditions and with the same glucose feed, the yield was 16.5% and the productivity was only 0.6 g/l/h.

Thus, for a given strain, the method of the invention achieved much better yield and productivity than the processes conventional employed.

Also, the low residual glucose content meant that the arabitol recovered was again of entirely satisfactory purity.

What is claimed:

1. A method of producing arabitol by continuous fermentation of at least one sugar by micro-organisms producing arabitol, comprising the following steps:
    a) arabitol is produced in a first fermentation area comprising at least one fermenter, in such a manner that some of the sugar introduced into the fermentation medium is consumed by said micro-organisms,
    b) some of the fermentation medium obtained in this way is transferred into a second fermentation area including at least one fermenter, the volume being maintained constant in the first fermentation area by adding sugar,
    c) production of arabitol is continued in said second fermentation area in such a manner as to consume the residual sugar of the fermentation medium,
    d) the fermentation medium thus obtained from said second fermentation area is separated continuously into a fraction concentrated in micro-organisms and another, soluble fraction enriched in arabitol, and
    e) the arabitol thus obtained is collected.

2. A method according to claim 1 wherein said fraction concentrated in micro-organisms is recycled to the entry of the first fermentation area.

3. A method according to claim 1 wherein the portion of the sugar consumed by the arabitol-producing micro-organisms in the first fermentation area is at least 50 wt. % of the sugar introduced into the fermentation medium.

4. A method according to claim 1 wherein the residual sugar content in the second fermentation area is not greater than 2 wt. %.

5. A method according to claim 1 wherein the fermenters of the second fermentation area have a volume less than the fermenters of the first area.

6. A method according to claim 5 wherein the first and second fermentation areas each comprise a single fermenter.

7. A method according to claim 1 wherein the arabitol-producing micro-organisms are selected from the group consisting of natural or modified osmosis-tolerant yeasts of the genus Yamadazyma, Debaromyces, Hansenula, Candida, Zygosaccharomyces or Saccharomyces.

8. A method according to claim 1 wherein the sugar is chosen from carbonaceous sources which can be assimilated directly by the arabitol-producing micro-organisms.

9. A method according to claim 3 wherein the portion of the sugar consumed by the arabitol-producing micro-organisms in the first fermentation area is at least 80 wt. % of the sugar introduced into the fermentation medium.

10. A method according to claim 9 wherein the portion of the sugar consumed by the arabitol-producing micro-organisms in the first fermentation area is at least 90 wt. % of the sugar introduced into the fermentation medium.

11. A method according to claim 4 wherein the residual sugar content in the second fermentation area is not greater than 1 wt. %.

12. A method according to claim 8 wherein the sugar is glucose.

* * * * *